(12) United States Patent
He et al.

(10) Patent No.: US 11,754,695 B2
(45) Date of Patent: Sep. 12, 2023

(54) ULTRASOUND IMAGING DEVICE

(71) Applicant: Wuxi Hisky Medical Technologies Co., Ltd., Wuxi (CN)

(72) Inventors: Qiong He, Wuxi (CN); Shibo Sun, Wuxi (CN); Jinhua Shao, Wuxi (CN); Jin Sun, Wuxi (CN); Houli Duan, Wuxi (CN)

(73) Assignee: WUXI HISKY MEDICAL TECHNOLOGIES CO., LTD., Wuxi (CN)

( * ) Notice: Subject to any disclaimer, the term of this patent is extended or adjusted under 35 U.S.C. 154(b) by 112 days.

(21) Appl. No.: 17/407,093

(22) Filed: Aug. 19, 2021

(65) Prior Publication Data

US 2021/0382156 A1    Dec. 9, 2021

Related U.S. Application Data

(63) Continuation of application No. PCT/CN2020/071098, filed on Jan. 9, 2020.

(30) Foreign Application Priority Data

Feb. 22, 2019    (CN) .......................... 201910133780.X

(51) Int. Cl.
*G01S 7/52*    (2006.01)
*A61B 8/00*    (2006.01)

(52) U.S. Cl.
CPC .......... *G01S 7/5208* (2013.01); *A61B 8/4254* (2013.01); *G01S 7/52053* (2013.01)

(58) Field of Classification Search
CPC .. G01S 7/5208; G01S 7/52053; A61B 8/4254
See application file for complete search history.

(56) References Cited

U.S. PATENT DOCUMENTS 9,274,088 B2    3/2016    Daft
9,282,945 B2    3/2016    Specht
(Continued)

FOREIGN PATENT DOCUMENTS

CN    101842718 A    9/2010
CN    102599931 A    7/2012
(Continued)

OTHER PUBLICATIONS

Extended European Search Report of parallel application EP20759626.3.

(Continued)

*Primary Examiner* — Dixomara Vargas
(74) *Attorney, Agent, or Firm* — J.C. PATENTS

(57) ABSTRACT

An ultrasound imaging device, including: a processor (10), N ultrasound systems (20), a communication channel (30) and an ultrasonic probe (40); where N is a positive integer greater than 1; the processor (10) is configured to receive an ultrasound system setting instruction input by a user, so that a ultrasound system (20) of the N ultrasound systems (20) is in an enabled state; the ultrasound system (20) in the enabled state is configured to send a control instruction to the ultrasonic probe (40) via the communication channel (30); and the ultrasonic probe (40) is configured to cooperate with the ultrasound system (20) in the enabled state to operate according to the control instruction.

20 Claims, 3 Drawing Sheets

(56) References Cited

U.S. PATENT DOCUMENTS

| | | | |
|---|---|---|---|
| 2007/0232924 A1 | 10/2007 | Karasawa | |
| 2008/0114239 A1* | 5/2008 | Randall | G01S 7/5208 |
| | | | 600/437 |
| 2009/0131786 A1 | 5/2009 | Amemiya | |
| 2010/0228130 A1* | 9/2010 | Chiang | A61B 8/4236 |
| | | | 600/447 |
| 2012/0190986 A1 | 7/2012 | Sato | |
| 2013/0281863 A1* | 10/2013 | Chiang | G01S 7/52063 |
| | | | 600/459 |
| 2014/0066778 A1 | 3/2014 | Nishiwaki | |
| 2014/0323869 A1 | 10/2014 | Jin | |
| 2014/0343429 A1* | 11/2014 | Jensen | A61B 8/4444 |
| | | | 600/443 |
| 2014/0378838 A1 | 12/2014 | Son | |
| 2015/0065881 A1* | 3/2015 | Cho | A61B 8/467 |
| | | | 600/443 |
| 2015/0313578 A1* | 11/2015 | Yu | A61B 8/4254 |
| | | | 600/459 |
| 2017/0071579 A1 | 3/2017 | Ko | |

FOREIGN PATENT DOCUMENTS

| | | |
|---|---|---|
| CN | 103377163 A | 10/2013 |
| CN | 103654848 A | 3/2014 |
| CN | 104546003 A | 4/2015 |
| CN | 105395218 A | 3/2016 |
| CN | 106662552 A | 5/2017 |
| CN | 108670304 A | 10/2018 |
| CN | 109805958 A | 5/2019 |
| JP | 2003079628 A | 3/2003 |
| JP | 2009112679 A | 5/2009 |
| JP | 2012065718 A | 4/2012 |
| JP | 2012152317 A | 8/2012 |
| JP | 2013121494 A | 6/2013 |
| JP | 2016182223 A | 10/2016 |
| JP | 6364955 B2 | 8/2018 |
| RU | 2010121932 A | 12/2011 |
| WO | WO2004041094 A2 | 5/2004 |

OTHER PUBLICATIONS

First Office Action of parallel application IN202117037959.
International Search Report of PCT/CN2020/071098.
Notice of Allowance of priority CN application 201910133780X.
First Office Action of priority CN application 201910133780X.
Notice of Allowance of the parallel application JP2021-549359.
First Office Action of the parallel application JP2021-549359.
First Office Action of the parallel application KR10-2021-7028245.
First Office Action of the parallel application RU2021126276.

* cited by examiner

ULTRASOUND IMAGING DEVICE

CROSS-REFERENCE TO RELATED DISCLOSURES

This disclosure is a continuation of International Application No. PCT/CN2020/071098, filed on Jan. 9, 2020, which claims priority to Chinese Patent Application No. 201910133780.X, filed on Feb. 22, 2019. Both of the aforementioned disclosures are hereby incorporated by reference in their entireties.

TECHNICAL FIELD

Embodiments of the present disclosure relate to ultrasound data transmission technology and, in particular, to a multi-ultrasound imaging device.

BACKGROUND

An ultrasound imaging method is widely used in clinical diagnosis and becomes a first choice for clinical diagnosis of various diseases. The ultrasound imaging method controls an ultrasonic probe to transmit and receive signals through a host of an ultrasound imaging device to accomplish the purpose of ultrasound imaging.

With the development of science and technology, researchers continue to improve an ultrasound imaging system and obtain an ultra-high-speed ultrasound imaging system that can support the requirement of ultra-high-speed imaging.

There are many differences between the ultrasound imaging system and the ultra-high-speed ultrasound imaging system. For example, the ultrasound imaging system mostly uses a line scan method for transmission, reception and imaging, while the ultra-high-speed ultrasound imaging system mostly uses a plane wave method for transmission, reception and imaging. For another example: the ultrasound imaging system and the ultra-high-speed ultrasound imaging system use different numbers of array elements and different imaging modes during operation, so that the excitation voltage of the ultrasonic probe is not completely consistent. In addition, the ultrasonic probe corresponding to a design of the ultra-high-speed ultrasound imaging system also has different requirements.

If it can be compatible with the ultra-high-speed ultrasound imaging system based on the original ultrasound imaging device, it can even support other ultrasound imaging systems presented in subsequent development, and can fully and effectively multiplex the components of the original ultrasound imaging device and provide an ultrasound imaging system with good compatibility, compact design and low cost, which will have very important and realistic scientific and economic value.

SUMMARY

An embodiment of the present disclosure provides an ultrasound imaging device, so as to realize a function that at least two imaging systems can be used in a same ultrasound imaging device.

The embodiment of the present disclosure provides an ultrasound imaging device, including: a processor, N ultrasound systems, a communication channel and an ultrasonic probe; where N is a positive integer greater than 1;

the processor is configured to receive an ultrasound system setting instruction input by a user, so that an ultrasound system of the N ultrasound systems is in an enabled state;

the ultrasound system in the enabled state is configured to send a control instruction to the ultrasonic probe via the communication channel; and the ultrasonic probe is configured to cooperate with the ultrasound system in the enabled state to operate according to the control instruction.

Optionally, the communication channel includes: a system multiplexing array and a sensor control array; where one side of the system multiplexing array is connected to the N ultrasound systems, the other side of the system multiplexing array is connected to one side of the sensor control array, and the other side of the sensor control array is connected to the ultrasonic probe;

one side of the system multiplexing array includes N groups of ports, where each group of ports are connected to the ultrasound system respectively;

the system multiplexing array is configured to send a state control instruction sent by the ultrasound system in the enabled state to the sensor control array; and the sensor control array is configured to send a received state control instruction sent by the ultrasound system in the enabled state to the ultrasonic probe.

Optionally, the system multiplexing array includes: a system multiplexing control unit and a system multiplexing connecting unit, and the system multiplexing connecting unit includes the N groups of ports; and the system multiplexing control unit is configured to control, according to the ultrasound system in the enabled state, a group of ports in the system multiplexing connecting unit corresponding to the ultrasound system in the enabled state to connect with the ultrasound system in the enabled state in a communicational way.

Optionally, the system multiplexing connecting unit is an array composed of a plurality of switches.

Optionally, the ultrasonic probe includes M array elements, where M is a positive integer greater than 1; the sensor control array includes a sensor control unit and a sensor connecting unit, and the sensor connecting unit is connected to the ultrasonic probe; and the sensor control unit is configured to control, according to the ultrasound system in the enabled state, the sensor connecting unit to operate with the array elements corresponding to the ultrasound system in the enabled state.

Optionally, the sensor connecting unit is an array composed of a plurality of switches.

Optionally, an operating mode of the sensor connecting unit is a one-to-many mode or a one-to-one mode; where the one-to-many mode represents that one switch of the sensor connecting unit is connected to at least two of the array elements; and the one-to-one mode represents that one switch of the sensor connecting unit is connected to one of the array elements.

Optionally, the N ultrasound systems are mutually independent hardware systems.

Optionally, the N ultrasound systems are integrated on a same hardware system.

Optionally, the ultrasound imaging device further includes: a display device;

the processor is configured to detect whether the ultrasonic probe is connected with the communication channel in a communicational way; if the ultrasonic probe is not connected with the communication channel, control the display device to display reminder information; and the display device is configured to display reminder information, and the reminder information is configured to remind that the ultrasonic probe is not connected with the communication channel in a communicational way.

The embodiment of the present disclosure provides an ultrasound imaging device. In the ultrasound imaging device provided with N ultrasound systems, a processor generates a control instruction that can instruct the current operating system of the ultrasound imaging device according to a user's setting instruction, and, through the control instruction, controls one ultrasound system of the N ultrasound systems to operate, that is, in the enabled state; and the ultrasound system in the enabled state generates a state control instruction according to the control instruction, and controls a communication channel for channel configuration, so that the configured communication channel can transmit the state control instruction generated by the ultrasound system in the enabled state to the ultrasonic probe, thereby controlling the ultrasonic probe to perform the operation corresponding to the state control instruction. And the ultrasonic probe feeds back feedback information to the ultrasound system in the enabled state through a configured communication channel. It is realized that when N ultrasound systems operate separately, they can perform the transmission of the state control instruction and the feedback information through the same communication channel, so that the ultrasound imaging device does not need to set up a communication channel for each of the N ultrasound systems separately, which improves functional compatibility of the ultrasound imaging device, and reduces the cost and volume of manufacturing an ultrasound imaging device.

BRIEF DESCRIPTION OF DRAWINGS

To describe the technical solutions in embodiments of the present disclosure or in the prior art more clearly, the following briefly introduces the accompanying drawings needed for describing the embodiments or the prior art. Obviously, the accompanying drawings in the following description are merely some embodiments of the present disclosure, and those of ordinary skilled in the art may still obtain other accompanying drawings based on these accompanying drawings without creative effort.

DESCRIPTION OF EMBODIMENTS

In order to make the objections, technical solutions, and advantages of the embodiments of the present disclosure clearer, the technical solutions of the embodiments of the present disclosure will be described clearly and completely below with reference to the accompanying drawings in the embodiments of the present disclosure. Obviously, the described embodiments are part of the embodiments of the present disclosure, rather than all of the embodiments. Based on the embodiments of the present disclosure, all other embodiments obtained by those of ordinary skilled in the art without creative effort shall fall within the protecting scope of the present disclosure.

Terms "first", "second", "third", "fourth", etc. (if any) in the description and claims as well as the above-mentioned accompanying drawings of the present application can be used to distinguish similar objects, and do not need to be used to describe a specific order or sequence.

In addition, it should be noted that, in the embodiments of the present disclosure, unless otherwise clearly specified and limited, the terms "connected", "connecting", etc. should be understood in a broad sense. For example, they may be a mechanical connection or an electrical connection, they may a direct connection or an indirect connection through an intermediate medium, and they can be an internal communication between two elements or an interaction relationship between two elements. Unless specifically defined otherwise, for those of ordinary skilled in the art, the specific meanings of the above-mentioned terms in the embodiments of the present disclosure can be understood according to specific circumstances.

Figure 1:
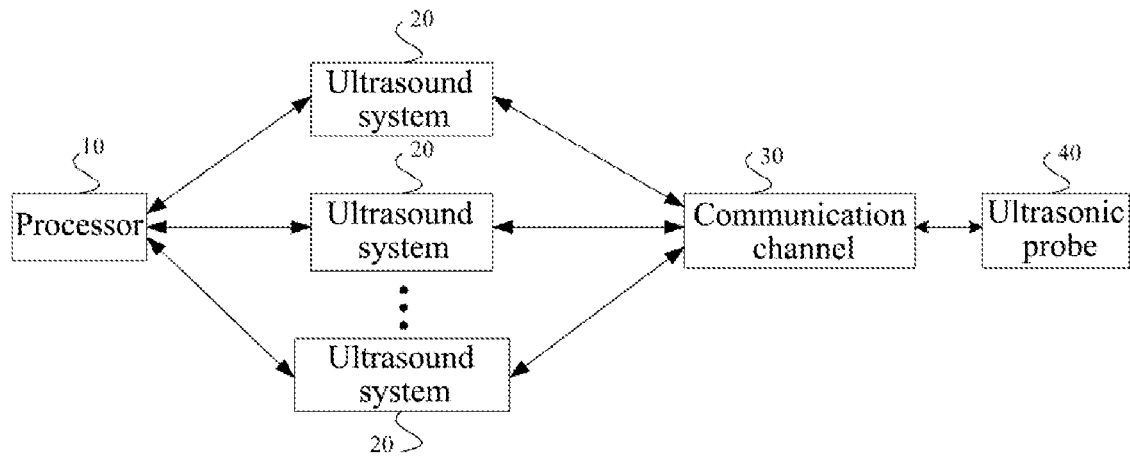
FIG. 1 is a schematic structural diagram of an ultrasound imaging device provided by an embodiment of the present disclosure.

FIG. 1 is a schematic structural diagram of an ultrasound imaging device provided by an embodiment of the present disclosure. As shown in FIG. 1, the ultrasound imaging device of this embodiment may include: a processor 10, N ultrasound systems 20, a communication channel 30, and an ultrasonic probe 40. Where N is a positive integer greater than 1.

The processor 10 is configured to receive an ultrasound system setting instruction input by a user, so that an ultrasound system 20 of the N ultrasound systems 20 is in an enabled state.

The ultrasound system in the enabled state is configured to send a control instruction to the ultrasonic probe 40 via the communication channel 30.

The ultrasonic probe 40 is configured to cooperate with the ultrasound system in the enabled state to operate according to the control instruction.

In this embodiment, the ultrasound imaging device includes N ultrasound systems 20, where the ultrasound imaging device including two ultrasound systems 20 is taken as an example for description in this embodiment. The two ultrasound systems are: a first ultrasound system and a second ultrasound system.

The ultrasound system setting instruction may be an ultrasound system setting instruction input by the user in real time according to current needs. For example, when the user currently needs to use the first ultrasound system, an instruction which can enable the first ultrasound system to be in the enabled state is input to the processor 10, and if the user would use the second ultrasound system then, an instruction that can enable the second ultrasound system to be in an enabled state would be input to the processor. The ultrasound system setting instruction may also be a use flow of the first ultrasound system and the second ultrasound system set by the user. For example, the time periods, during which the first ultrasound system and the second ultrasound system are in the enabled state, are set respectively. Where the first ultrasound system and the second ultrasound system cannot be in the enabled state at the same time, that is, the first ultrasound system and the second ultrasound system cannot be used at the same time.

After the processor 10 obtains the ultrasound system setting instruction input by the user, a current operating system of the ultrasound imaging device is determined according to the ultrasound system setting instruction, where the current operating system is the ultrasound system in the enabled state of the two ultrasound systems 20 of the ultrasound imaging device, the control instruction corresponding to the ultrasound system in the enabled state is generated, and the control instruction is sent to the ultrasound system in the enabled state.

Optionally, the ultrasound imaging device may further include: a control channel 50. The control channel 50 is configured to transmit the control instruction to the ultrasound system in the enabled state.

It can be understood that the processor 10 can send the control instruction to the first ultrasound system or the second ultrasound system using the same control channel 50, or send the control instruction to the first ultrasound system or the second ultrasound system using mutually independent control channels 50. When the same control channel 50 is used, the control channel 50 may be a high-speed serial computer expansion bus standard (Peripheral Component Interconnect Express, PCIe) cable or a USB interface. When the mutually independent control channels 50 are used, the mutually independent control channels 50 may be PCIe cables or USB interfaces at the same time, or one of them is a PCIe cable and the other is a USB interface.

If the first ultrasound system receives the control instruction sent by the processor 10, and the first ultrasound system is in the enabled state, according to the control instruction, a state control instruction that can control the operating state of the ultrasonic probe 40 to correspond to the first ultrasound system is generated, and the communication channel 30 is controlled to perform channel configuration, so that it can send the state control instruction corresponding to the first ultrasound system to the ultrasonic probe 40. If the second ultrasound system receives the control instruction sent by the processor 10, and the second ultrasound system is in the enabled state, according to the control instruction, a state control instruction that can control the operating state of the ultrasonic probe 40 to correspond to the second ultrasound system is generated, and the communication channel 30 is controlled to perform channel configuration, so that it can send the state control instruction corresponding to the second ultrasound system to the ultrasonic probe 40.

After receiving the state control instruction, the ultrasonic probe 40 cooperates with the ultrasound system in the enabled state to work according to the state control instruction.

In this embodiment, in the ultrasound imaging device provided with N ultrasound systems, a processor generates a control instruction that can instruct the current operating system of the ultrasound imaging device according to a user's setting instruction, and, through the control instruction, controls one ultrasound system of the N ultrasound systems to operate, that is, in the enabled state; and the ultrasound system in the enabled state generates a state control instruction according to the control instruction, and controls a communication channel for channel configuration, so that the configured communication channel can transmit the state control instruction generated by the ultrasound system in the enabled state to the ultrasonic probe, thereby controlling the ultrasonic probe perform the operation corresponding to the state control instruction. And the ultrasonic probe feeds back feedback information to the ultrasound system in the enabled state through a configured communication channel. It is realized that when N ultrasound systems operate separately, they can perform the transmission of the state control instruction and the feedback information through the same communication channel, so that the ultrasound imaging device does not need to set up a communication channel for each of the N ultrasound systems separately, which improves functional compatibility of the ultrasound imaging device, and reduces the cost and volume of manufacturing an ultrasound imaging device.

Figure 2:
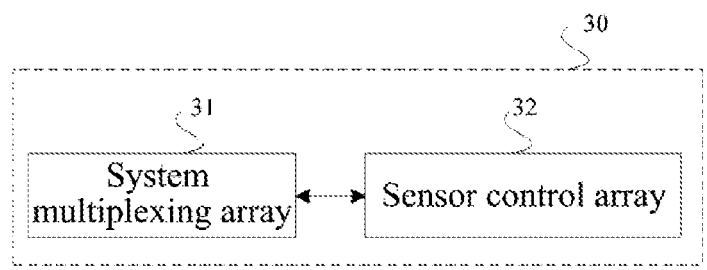
FIG. 2 is a schematic structural diagram of a communication channel provided by an embodiment of the present disclosure.

Optionally, FIG. 2 is a schematic structural diagram of a communication channel provided by an embodiment of the present disclosure. As shown in the figure, based on the embodiment shown in FIG. 1, the communication channel 30 includes: a system multiplexing array 31, and a sensor control array 32; where one side of the system multiplexing array 31 is connected to the N ultrasound systems 20, the other side of the system multiplexing array 31 is connected to one side of the sensor control array 32, and the other side of the sensor control array 32 is connected to the ultrasonic probe 40.

One side of the system multiplexing array 31 includes N groups of ports, where each group of ports is connected to an ultrasound system 20.

The system multiplexing array 31 is configured to send a state control instruction sent by the ultrasound system in the enabled state to the sensor control array 32.

The sensor control array 32 is configured to send the received state control instruction sent by the ultrasound system in the enabled state to the ultrasonic probe 40.

In this embodiment, the ultrasound system that receives the control instruction among the first ultrasound system and the second ultrasound system starts to operate. For example, if the first ultrasound system receives the control instruction, the first ultrasound system is in the enabled state, generates a state control instruction according to the control instruction, and controls the connection between the system multiplexing array 31 and the first ultrasound system, the connection state between the system multiplexing array 31 and the sensor control array 32, and the connection state between the sensor control array 32 and the ultrasonic probe 40. Therefore, the multiplexing array 31 and the sensor control array 32 can transmit the state control instruction generated by the first ultrasound system to the ultrasonic probe 40.

Figure 3:
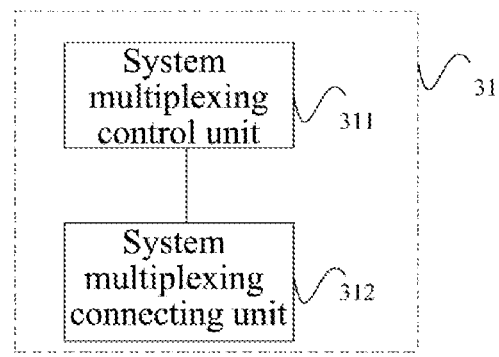
FIG. 3 is a schematic structural diagram of a system multiplexing array provided by an embodiment of the present disclosure.

Optionally, FIG. 3 is a schematic structural diagram of a system multiplexing array provided by an embodiment of the present disclosure. As shown in FIG. 3, on the basis of the above embodiments, the system multiplexing array 31 includes: a system multiplexing control unit 311 and a system multiplexing connecting unit 312, and the system multiplexing connecting unit 312 includes the N groups of ports.

The system multiplexing control unit 311 is configured to control, according to the ultrasound system in the enabled state, a group of ports in the system multiplexing connecting unit 312 corresponding to the ultrasound system in the enabled state to connect with the ultrasound system in the enabled state in a communicational way.

Specifically, the system multiplexing connecting unit 312 includes the N groups of ports, and each group of ports is configured to connect with one of the N ultrasound systems 20.

When the ultrasound imaging device includes two ultrasound systems, that is, the ultrasound imaging device includes a first ultrasound system and a second ultrasound system, the system multiplexing control unit 311 is controlled by the ultrasound system in the enabled state in the first ultrasound system and the second ultrasound system, and the system multiplexing control unit 311 controls the connection state of the two ports in the system multiplexing connecting unit 312, to enable only one port of the two ports of the system multiplexing connecting unit 312 to be connected at the same time. Where the number of ports included in the system multiplexing connecting unit 312 is greater than or equal to the number of ultrasound systems included in the ultrasound imaging device. That is, the system multiplexing control unit 311 determines that the ultrasound system in the enabled state is the first ultrasound system, and the port, used to connect to the first ultrasound system among the ports of the system multiplexing connecting unit 312, is controlled to connect to the first ultrasound system. If the ultrasound system in the enabled state is determined to be the second ultrasound system, the port, used to connect to the second ultrasound system among the ports of the system multiplexing connecting unit 312, is controlled to connect to the first ultrasound system. Therefore, the system multiplexing array 31 can only receive the state control instruction sent by the first ultrasound system or the second ultrasound system at the same time, and send the state control instruction to the sensor control array 32.

Figure 4:
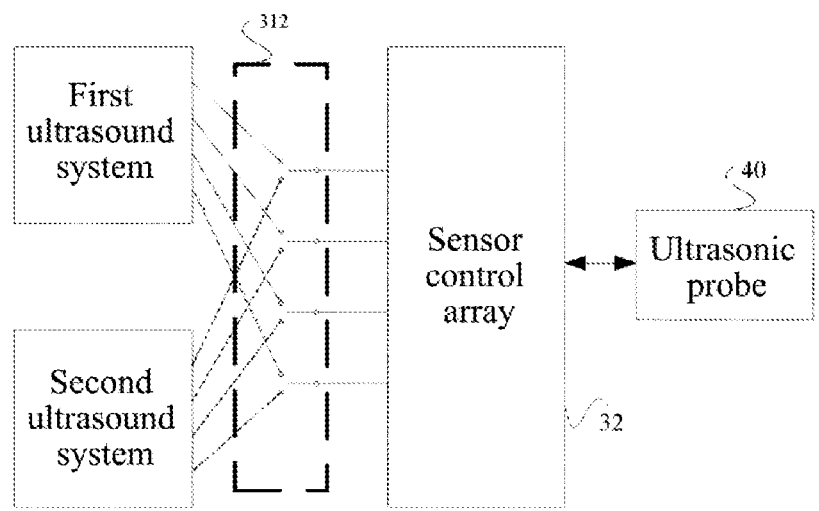
FIG. 4 is a schematic diagram of a connection of a system multiplexing connecting unit provided by an embodiment of the present disclosure.

Optionally, FIG. 4 is a schematic diagram of a connection of a system multiplexing connecting unit provided by an embodiment of the present disclosure. As shown in FIG. 4, the system multiplexing connecting unit 312 is an array composed of a plurality of switches. Where the ultrasound imaging device shown in FIG. 4 includes two ultrasound systems, the two ultrasound systems are the first ultrasound system and the second ultrasound system, and the system multiplexing connecting unit 312 includes 4 switches.

Specifically, when the ultrasound system in the enabled state is the first ultrasound system, the first ultrasound system controls the system multiplexing control unit 311, so that the system multiplexing control unit 311 controls the switch in the system multiplexing connecting unit 312 to connect with the first ultrasound system. When the ultrasound system in the enabled state is the second ultrasound system, the system multiplexing control unit 311 controls the switch in the system multiplexing connecting unit 312 to connect to the second ultrasound system. In this way, the system multiplexing array 31 can be connected with the first ultrasound system or can also be connected with the second ultrasound system. In addition, through the system multiplexing array 31, the first ultrasound system and the second ultrasound system can operate in different transmitting, receiving, and imaging modes, and the first ultrasound system and the second ultrasound system are not affected by each other's excitation voltage.

Figure 5:
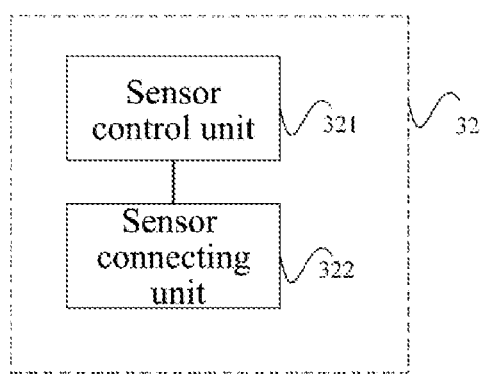
FIG. 5 is a schematic structural diagram of a sensor control array provided by an embodiment of the present disclosure.

Optionally, FIG. 5 is a schematic structural diagram of a sensor control array provided by an embodiment of the present disclosure. As shown in FIG. 5, on the basis of each of the above embodiments, the ultrasonic probe includes M array elements, where M is a positive integer greater than 1; and the sensor control array 32 includes a sensor control unit 321 and a sensor connecting unit 322, where the sensor connecting unit 322 is connected to the ultrasonic probe 40.

The sensor control unit 321 is configured to control, according to the current operating system, operation of the sensor connecting unit 322 and the array element corresponding to the current operating system.

Specifically, the sensor control unit 321 is controlled by the ultrasound system in the enabled state, and the sensor control unit 321 controls the operating mode of the sensor connecting unit 322, that is, controls the array element corresponding to the ultrasound system in the enabled state in the sensor connecting unit 322 to operate, and transmits the state control instruction to the array element corresponding to the ultrasound system in the enabled state in the ultrasonic probe 40, to enable the array element to operate according to the state control instruction. It is realized that the state control instruction is sent to the array element corresponding to the ultrasound system in the enabled state through the sensor control array 32, so that the array element operates according to the state control instruction sent by the ultrasound system in the enabled state.

Optionally, the sensor connecting unit 322 is an array composed of a plurality of switches.

Specifically, the process of the sensor connecting unit 322 transmitting the state control instruction is that: the system multiplexing array 31 transmits the state control instruction to the sensor connecting unit 322 through an output port of the system multiplexing connecting unit 312, and after the sensor control array 32 receives the state control instruction, the state control instruction is sent to the ultrasonic probe 40 through the switch closed in the sensor connecting unit 322.

Optionally, the operating mode of the sensor connecting unit 322 is a one-to-many mode or a one-to-one mode; where the one-to-many mode represents that one switch in the sensor connecting unit 322 can be connected to at least two of the array elements; and the one-to-one mode represents that one switch of the sensor connecting unit 322 is connected to one of the array elements.

Figure 6:
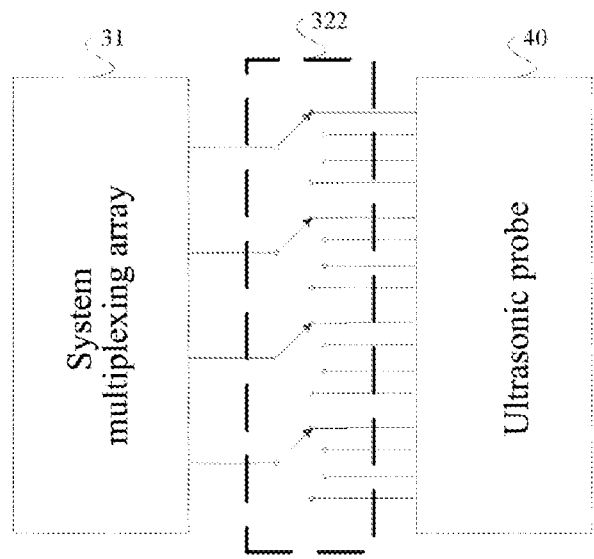
FIG. 6 is a schematic diagram of a one-to-many operating mode of a sensor connecting unit provided by an embodiment of the present disclosure.

FIG. 6 is a schematic diagram of a one-to-many operating mode of a sensor connecting unit provided by an embodiment of the present disclosure. As shown in FIG. 6, the sensor connecting unit 322 is located between the system multiplexing array 31 and the ultrasonic probe 40, and is used to connect the system multiplexing array 31 and the ultrasonic probe 40. One end of a switch of the sensor connecting unit 322 is connected to one end of the system multiplexing array 31, and the other end is connected to the interface of the four array elements in the ultrasonic probe 40. When it is determined that the current operating system is the first ultrasound system, the first ultrasound system controls the sensor control unit 321 so that the sensor control unit 321 controls any switch in the sensor connecting unit 322 to connect the system multiplexing array 31 with the corresponding array element of the four array elements, so as to control the operation of the corresponding array element.

When it is determined that the current operating system is the second ultrasound system, the working principle and process of the sensor connecting unit 322 can refer to the description when the current operating system is the first ultrasound system, which will not be repeated here.

Figure 7:
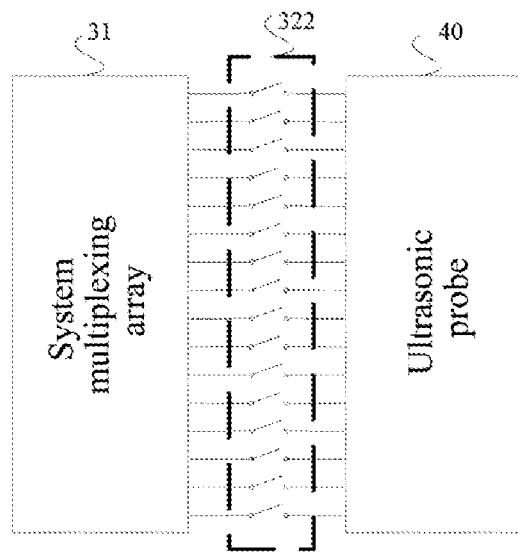
FIG. 7 is a schematic diagram of a one-to-one operating mode of a sensor connecting unit provided by an embodiment of the present disclosure.

FIG. 7 is a schematic diagram of a one-to-one operating mode of a sensor connecting unit provided by an embodiment of the present disclosure. As shown in FIG. 7, one end of a switch of the sensor connecting unit 322 is connected to one end of the system multiplexing array 31, and the other end of a switch of the sensor connecting unit 32 is connected to an interface of an array element in the ultrasonic probe 40. When it is determined that the current operating system is the first ultrasound system, the first ultrasound system controls the sensor control unit 321 to enable the sensor control unit 321 to control the closed state of any switch of the sensor connecting unit 322, that is, when one of the array elements needs to be used, the switch connected to the array element is closed, so that the system multiplexing array 31 is connected to the array element related to the ultrasound system in the enabled state, thereby realizing the control of the operation of the corresponding array element.

Optionally, the N ultrasound systems 20 in the ultrasound imaging device may be mutually independent hardware systems.

Optionally, the N ultrasound systems 20 in the ultrasound imaging device can be integrated on the same hardware system.

Optionally, the ultrasound imaging device further includes: a display device.

The processor is configured to detect whether the ultrasonic probe 40 connect with the communication channel 30 in a communicational way; and if the ultrasonic probe is not connected with the communication channel in a communicational way, control the display device to display reminder information.

The display device is configured to display reminder information, and the reminder information is configured to remind that the ultrasonic probe 40 is not connected with the communication channel 30.

Specifically, the communication channel 30 may be configured to transmit a state signal, the state signal represents the operating state of the ultrasonic probe 40, and different operating states correspond to different state signals. For example, when the ultrasonic probe 40 is not connected with the communication channel 30, the state signal is 00; when operating according to the state control instruction of the first ultrasound system, the state signal is 01; and when operating according to the state control instruction of the second ultrasound system, the state signal is 10. Where the operating state of the ultrasonic probe 40 is that the ultrasonic probe 40 is not connected with the communication channel 30, or operates according to the state control instruction of the first ultrasound system, or operates according to the state control instruction of the second ultrasound system.

When the ultrasonic imaging device system is initialized, the operating state of the ultrasonic probe 40 needs to be detected firstly. Where the communication channel 30 can actively transmit the state signal to the processor 10, and the processor 10 judges the operating state of the ultrasonic probe 40 according to the received state signal; and an inquiry signal can be also sent to the ultrasonic probe 40 through the processor 10. There are different response signals for different operating status of the ultrasonic probe 40, and the processor 10 judges the operating state of the ultrasonic probe 40 according to the received response signal.

When the processor 10 detects that the ultrasonic probe 40 is not connected with the communication channel 30, a reminder information is displayed on the display to remind the user that the ultrasonic probe 40 is not connected to the communication channel 30, and the ultrasonic probe 40 needs to be connected with the communication channel 30.

Optionally, the first ultrasound system in the above embodiments may be an ultrasound imaging system, and the second ultrasound system may be an ultra-high-speed ultrasound imaging system.

Finally, it should be illustrated that the above embodiments are only used to illustrate the technical solutions of the present disclosure, rather than limiting it; although the present disclosure has been illustrated in detail with reference to the foregoing each embodiment, those of ordinary skilled in the art should understand that it is still possible to modify the technical solutions described in the foregoing embodiments, or equivalently replace part or all of the technical features; and these modifications or replacements do not cause the essence of the corresponding technical solutions to deviate from the scope of the technical solution of each embodiment of the present disclosure.

What is claimed is:

1. An ultrasound imaging device, comprising: a processor, N ultrasound systems, a communication channel and an ultrasonic probe; wherein N is a positive integer greater than 1;
   the processor is configured to receive an ultrasound system setting instruction input by a user, so that an ultrasound system of the N ultrasound systems is in an enabled state;
   the ultrasound system in the enabled state is configured to send a state control instruction to the ultrasonic probe via the communication channel, wherein when the N ultrasound systems operate separately, the N ultrasound systems perform transmission of the state control instruction through a same communication channel; and
   the ultrasonic probe is configured to cooperate with the ultrasound system in the enabled state to operate according to the state control instruction.

2. The device according to claim 1, wherein the communication channel comprises: a system multiplexing array and a sensor control array; wherein one side of the system multiplexing array is connected to the N ultrasound systems, the other side of the system multiplexing array is connected to one side of the sensor control array, and the other side of the sensor control array is connected to the ultrasonic probe;
   one side of the system multiplexing array comprises N groups of ports, wherein each group of ports are connected to the ultrasound system respectively;
   the system multiplexing array is configured to send the state control instruction sent by the ultrasound system in the enabled state to the sensor control array; and
   the sensor control array is configured to send a received state control instruction sent by the ultrasound system in the enabled state to the ultrasonic probe.

3. The device according to claim 2, wherein the system multiplexing array comprises: a system multiplexing control unit and a system multiplexing connecting unit, and the system multiplexing connecting unit comprises the N groups of ports; and
   the system multiplexing control unit is configured to control, according to the ultrasound system in the enabled state, a group of ports in the system multiplexing connecting unit corresponding to the ultrasound system in the enabled state to connect with the ultrasound system in the enabled state in a communicational way.

4. The device according to claim 3, wherein the system multiplexing connecting unit is an array composed of a plurality of switches.

5. The device according to claim 2, wherein the ultrasonic probe comprises M array elements, wherein M is a positive integer greater than 1; the sensor control array comprises a sensor control unit and a sensor connecting unit, and the sensor connecting unit is connected to the ultrasonic probe; and
   the sensor control unit is configured to control, according to the ultrasound system in the enabled state, the sensor connecting unit to operate with the array elements corresponding to the ultrasound system in the enabled state.

6. The device according to claim 5, wherein the sensor connecting unit is an array composed of a plurality of switches.

7. The device according to claim 6, wherein an operating mode of the sensor connecting unit is a one-to-many mode or a one-to-one mode; wherein the one-to-many mode represents that one switch of the sensor connecting unit is connected to at least two of the array elements; and the one-to-one mode represents that one switch of the sensor connecting unit is connected to one of the array elements.

8. The device according to claim 1, wherein the N ultrasound systems are mutually independent hardware systems.

9. The device according to claim 2, wherein the N ultrasound systems are mutually independent hardware systems.

10. The device according to claim 3, wherein the N ultrasound systems are mutually independent hardware systems.

11. The device according to claim 4, wherein the N ultrasound systems are mutually independent hardware systems.

12. The device according to claim 5, wherein the N ultrasound systems are mutually independent hardware systems.

13. The device according to claim 1, wherein the N ultrasound systems are integrated on a same hardware system.

14. The device according to claim 2, wherein the N ultrasound systems are integrated on a same hardware system.

15. The device according to claim 3, wherein the N ultrasound systems are integrated on a same hardware system.

16. The device according to claim 5, wherein the N ultrasound systems are integrated on a same hardware system.

17. The device according to claim 1, wherein the device further comprises: a display device;
   the processor is configured to detect whether the ultrasonic probe is connected with the communication channel in a communicational way; if the ultrasonic probe is not connected with the communication channel in a communicational way, control the display device to display reminder information; and
   the display device is configured to display reminder information, and the reminder information is configured to remind that the ultrasonic probe is not connected with the communication channel.

18. The device according to claim 2, wherein the device further comprises: a display device;
   the processor is configured to detect whether the ultrasonic probe is connected with the communication channel in a communicational way; if the ultrasonic probe is not connected with the communication channel in a communicational way, control the display device to display reminder information; and
   the display device is configured to display reminder information, and the reminder information is configured to remind that the ultrasonic probe is not connected with the communication channel.

19. The device according to claim 3, wherein the device further comprises: a display device;
   the processor is configured to detect whether the ultrasonic probe is connected with the communication channel in a communicational way; if the ultrasonic probe is not connected with the communication channel in a communicational way, control the display device to display reminder information; and
   the display device is configured to display reminder information, and the reminder information is configured to remind that the ultrasonic probe is not connected with the communication channel.

20. The device according to claim 5, wherein the device further comprises: a display device;
   the processor is configured to detect whether the ultrasonic probe is connected with the communication channel in a communicational way; if the ultrasonic probe is not connected with the communication channel in a communicational way, control the display device to display reminder information; and
   the display device is configured to display reminder information, and the reminder information is configured to remind that the ultrasonic probe is not connected with the communication channel.

* * * * *